United States Patent [19]

Petersen et al.

[11] 4,048,058

[45] Sept. 13, 1977

[54] METHODS TO BE USED IN REFORMING PROCESSES EMPLOYING MULTI-METALLIC CATALYSTS

[75] Inventors: Richard D. Petersen, Valparaiso, Ind.; Rodney L. Mieville, Evanston, Ill.

[73] Assignee: Standard Oil Company (Indiana), Chicago, Ill.

[21] Appl. No.: 621,047

[22] Filed: Oct. 9, 1975

[51] Int. Cl.$^2$ .................... C10G 35/08; B01J 27/02
[52] U.S. Cl. .................... 208/138; 208/139; 252/439
[58] Field of Search ............... 208/138, 139; 252/439

[56] References Cited

U.S. PATENT DOCUMENTS

| | | | |
|---|---|---|---|
| 2,863,825 | 12/1958 | Engel | 208/138 |
| 3,296,119 | 1/1967 | Bicek | 208/139 |
| 3,441,500 | 4/1969 | Wunderlich | 252/439 |
| 3,442,796 | 5/1969 | Hayes | 252/439 |
| 3,477,963 | 11/1969 | Venrooy | 252/439 |
| 3,617,520 | 11/1971 | Kluksdahl | 208/138 |
| 3,658,691 | 4/1972 | Keith et al. | 208/139 |
| 3,725,249 | 4/1973 | Vesely et al. | 208/139 |
| 3,801,498 | 4/1974 | Ransch | 208/139 |
| 3,897,328 | 7/1975 | Mitchell | 208/139 |
| 3,915,894 | 10/1975 | Clements et al. | 252/439 |
| 3,933,622 | 1/1976 | Mitchell et al. | 252/439 |

*Primary Examiner*—Delbert E. Gantz
*Assistant Examiner*—James W. Hellwege
*Attorney, Agent, or Firm*—James L. Wilson; Arthur G. Gilkes; William T. McClain

[57] ABSTRACT

There are disclosed a method for sulfiding a multi-metallic catalyst or a bi-metallic catalyst and a method for initiating the reforming of a petroleum hydrocarbon feedstock in a reforming reaction zone containing a multi-metallic catalyst or a bi-metallic catalyst.

The method for sulfiding is employed when a hydrogen-rich gas containing light hydrocarbons is used in the sulfiding of the catalyst. The method comprises passing a stream of said gas over said catalyst at a temperature of about 350° F. to about 470° F., injecting a sulfur-containing compound into the stream of gas upstream from said catalyst in order to provide a sulfur-carrying gas, and contacting said catalyst with said sulfur-carrying gas at said temperature for a time that is sufficient to provide a sulfur concentration on said catalyst of about 0.1 to about 2.5 moles of sulfur per mole of total active metal. A typical sulfur-containing compound is dimethyl sulfide.

39 Claims, 1 Drawing Figure

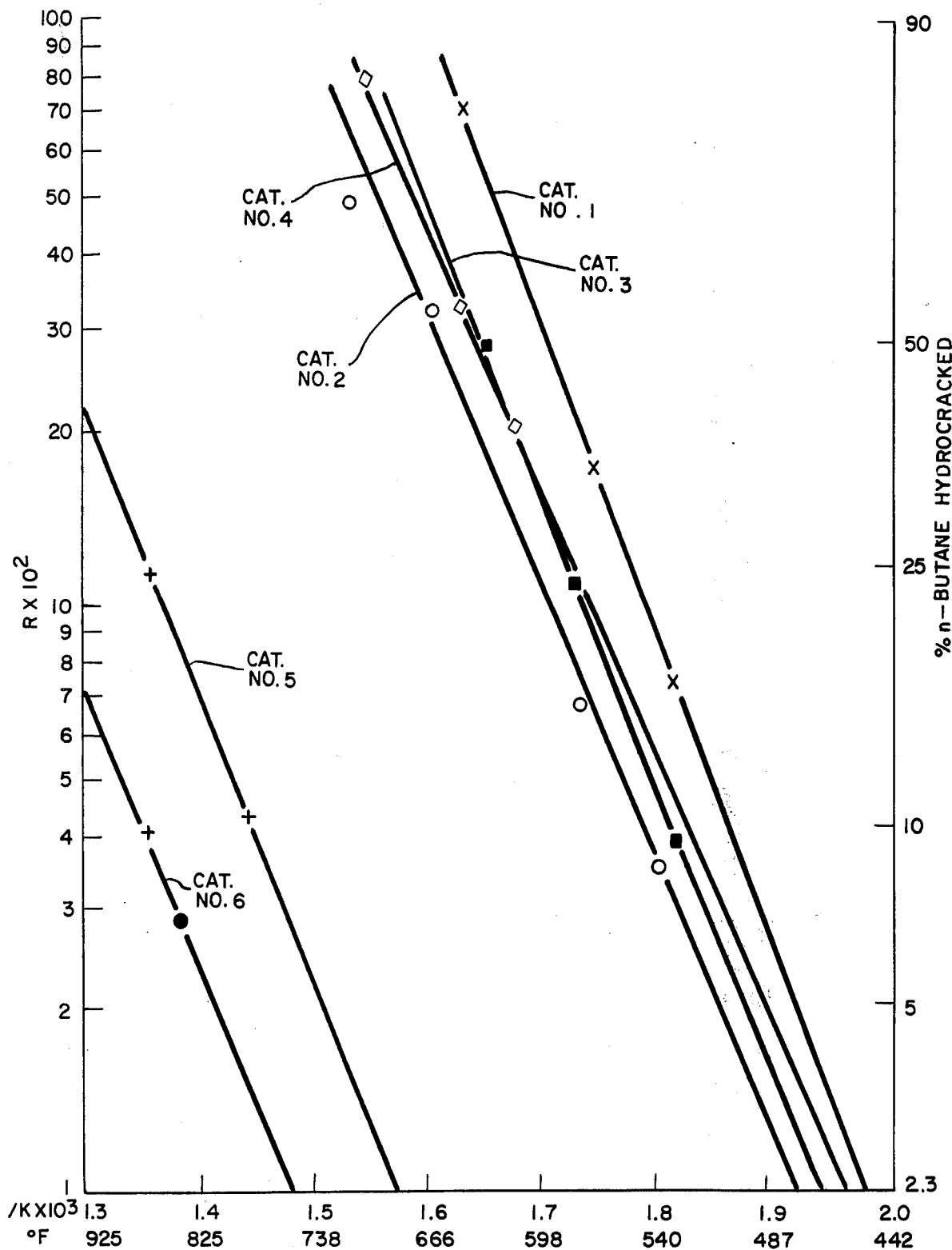

METHODS TO BE USED IN REFORMING PROCESSES EMPLOYING MULTI-METALLIC CATALYSTS

BACKGROUND OF THE INVENTION

The reforming of petroleum hydrocarbon streams is one of the important petroleum refining processes that may be employed to provide high-octane-number hydrocarbon blending components for gasoline. Although various reforming catalysts have been employed during the history of the reforming process, the preferred reforming catalyst is a catalyst containing a Group VIII noble metal, such as platinum. Recently, the preferred reforming catalysts are the bi-metallic an multi-metallic reforming catalysts which employ various combinations of hydrogenation metals, such as platinum-iridium, platinum-rhenium, platinum-gallium, and iridium-gold. Many of these bi-metallic and multi-metallic catalysts require sulfiding prior to their use for reforming in order to eliminate, or at least minimize, the excessive hydrocracking that occurs at the start of the reforming operation with a fresh catalyst or a regenerated catalyst.

Generally, the start-up procedure for a reforming process employing a platinum catalyst comprises heating the reactor to about 800° F. in the presence of a circulating gas under pressure. This circulating gas can be either natural gas or a recycle gas from another reformer. Such recycle gas contains hydrogen and light hydrocarbons. In general, such gas may contain anywhere from 70 to 80 weight percent hydrogen. When the reactor temperature has reached 800° F., the naphtha feedstock is introduced into the reaction zone and hydrogen is produced immediately.

When a bi-metallic or multi-metallic catalyst is employed, hydrocracking of the light hydrocarbons will occur during the heating-up period with the recycle gas and during the naphtha flow. It has been found that a sulfiding pretreatment of the catalyst will greatly reduce such initial excesive hydrocracking. Generally, sulfiding procedures require reduction of the catalyst with pure hydrogen at high temperatures, for example, 700° F. or above, and then subsequent sulfiding with hydrogen sulfide or other sulfur compounds at such high temperature. The use of such pure hydrogen is expensive. Moreover, when the gas is circulated to heat the catalyst bed, the gas will pich up hydrocarbons from the liquid in the high-pressure separator being used in the system. These hydrocarbons will then be hydrocracked during the heating-up period that is conducted for the multi-metallic catalyst.

There has now been discovered a method for sulfiding a bi-metallic or multi-metallic catalyst when employing a hydrogen-rich gas containing light hydrocarbons. Such method may be used conveniently as the sulfiding pretreatment step in the start-up or initial operation of a reforming process unit employing a bi-metallic or a multi-metallic catalyst. Hence, there has also been discovered a method for initiating the reforming of a petroleum hydrocarbon stream in a reforming reaction zone containing a multi-metallic or bi-metallic catalyst, when a hydrogen-rich gas containing light hydrocarbons is used. These methods, although using impure hydrogen, eliminate, or at least minimize, the above-described difficulties.

SUMMARY OF THE INVENTION

According to the present invention, there is provided a method for sulfiding a bi-metallic or multi-metallic catalyst when employing a hydrogen-rich gas that also contains light hydrocarbons. This method can be employed conveniently in the start-up of a hydrocarbon reforming process that utilizes a bi-metallic or a multi-metallic catalyst, such as a platinum-rhenium catalyst.

Broadly, the method for sulfiding comprises passing a stream of a hydrogen-rich gas containing light hydrocarbons over the catalyst at a temperature of about 350° F. to about 470° F., injecting a sulfur-containing compound into said stream up-stream from said catalyst in order to provide a sulfur-carrying gas and contacting said catalyst with said sulfur-carrying gas at said temperature for a time that is sufficient to provide a sulfur concentration on said catalyst of about 0.1 to about 2.5 moles of sulfur per mole of total active metal.

The sulfiding method of the present invention may comprise further passing the stream of hydrogen-rich gas containing light hydrocarbons over the catalyst at ambient temperature and then increasing the temperature to a value within the range of about 350° F. to about 470° F. while the gas is passing over the catalyst, each of these steps being performed prior to passing the gas over the catalyst at a temperature of about 350° F. to about 470° F.

The concentration of sulfur in the sulfur-carrying gas is about 0.01 to about 10 moles of sulfur per 100 moles of gas. The gas flow rate of hydrogen-rich gas is about 0.25 to about 100 standard cubic feet (SCF) of gas per pound of catalyst.

A preferred sulfur-containing compound is dimethyl sulfide.

According to the present invention, there is provided also a method for initiating the reforming of a petroleum hydrocarbon feedstock in a reforming reaction zone containing a multi-metallic catalyst or a bimetallic catalyst, which method comprises introducing a stream of hydrogen-rich gas containing light hydrocarbons into said reaction zone at a pressure of about 0 to about 1,000 psig, passing said stream through said reaction zone, adjusting the temperature in said reaction zone to a value of about 350° F. to about 470° F., injecting a sulfur-containing compound into said stream up-stream from said catalyst in order to provide a sulfur-carrying gas, contacting said catalyst with said sulfur-carrying gas at said temperature and at a gas flow rate of about 0.25 to about 100 SCF per pound of catalyst for a time that is sufficient to provide a sulfur concentration on said catalyst of about 0.1 to about 2.5 moles of sulfur per mole of total active metal, when sufficient sulfiding has occurred, discontinuing the injection of said sulfur-containing compound into said stream, adjusting the temperature, pressure, and hydrogen-rich-gas flow rate in said reaction zone to values that are to be used during the reforming operation, and introducing said feedstock into said reaction zone.

BRIEF DESCRIPTION OF THE DRAWING

An Arrhenius-type plot providing the amount of hydrocracking of n-butane over a catalyst comprising platinum and rhenium on an alumina is presented in the accompanying drawing.

DESCRIPTION AND PREFERRED EMBODIMENTS

The highly mechanized society of today requires increasing quantities of very high-octane-number motor fuels. The reforming process is especially advantageous for the production of high-octane-number blending component for motor fuels by means of the conversion of petroleum naphthas and petroleum hydrocarbon streams boiling in the gasoline boiling range. Such reforming proceses may be employed suitably either to produce high-octane-number blending components for unleaded and/or low-lead motor fuels or to provide additional aromatics for use in the chemical industries.

The present invention is directed to the starting up or initiating of a reforming process employing a bi-metallic or a multi-metallic reforming catalyst and to a pretreatment method for sulfiding the catalyst, which sulfiding method constitutes a portion of the start up of a reforming process employing a bi-metallic or a multi-metallic reforming catalyst.

According to the invention, there is provided a method for sulfiding a multi-metallic catalyst when employing a hydrogen-rich gas containing light hydrocrbons, the various metals of said catalyst comprising the total active metal of said catalyst. Broadly, this method comprises passing a stream of said gas over said catalyst at a temperature of about 350° F. to about 470° F., injecting a sulfur-containing compound into said stream up-stream from said catalyst in order to provide a sulfur-carrying gas, and contacting said catalyst with said sulfur-carrying gas at said temperature for a time that is sufficient to provide a sulfur concentration on said catalyst of about 0.1 to about 2.5 moles of sulfur per mole of total active metal.

Typical multi-metallic reforming catalysts are those containing a hydrogenation component, such as a Group VIII noble metal, in combination with a metal such as rhenium or gallium. In some cases, the multi-metallic catalyst may contain two Group VIII noble metals, such as platinum and iridium. The preferred Group VIII noble metal is platinum. Such Group VIII noble metal is present in an amount of about 0.05 weight percent to about 2 weight percent, calculated as the element and based upon the total weight of the catalyst. The additional metallic component, such as rhenium and/or gallium is present in an amount from about 0.05 weight percent to about 3 weight percent, calculated as the element and based upon the total weight of the catalyst. A typical multi-metallic catalyst is one which contains about 0.05 weight percent to about 2 weight percent platinum and about 0.05 weight percent to about 3 weight percent rhenium. While pltinum is the preferred Group VIII noble metal, other Group VIII noble metals, such as ruthenium, rhodium, palladium, osmium, or irridium may be employed.

The various metals of such a catalyst, e.g., the Group VIII noble metal, rhenium, gallium, and the like, make up the total active metal of the catalyst.

Typically, the multi-metallic reforming catalyst contains a solid catalytic support, which comprises a porous refractory inorganic oxide. The preferred refractory inorganic oxide is a catalytically active alumina, such as gamma-alumina, eta-alumina, or mixtures thereof. Such aluminas will have an average pore diameter of about 70 Angstrom units (A) to about 200 A, or larger. The alumina will hve a surface area of at least 80 square meters per gram and suitably should have a surface area of at least 150 square meters per gram. Preferred surface areas for such aluminas will fall within the range of about 170 to about 800 square meters per gram, or larger.

The solid catalytic support of the multi-metallic reforming catalyst may also contain a crystalline aluminosilicate material. Such a crystalline aluminosilicate material possesses uniform pores having a diameter within the range of about 5 A to about 16 A. A typical example is mordenite. Suitably, the crystalline aluminosilicate material in a finely-divided form is suspended in a distributed throughout a matrix of the porous refractory inorganic oxide. The aluminosilicate material may be present in an amount of about 0.5 weight percent to about 25 weight percent, based upon the weight of the catalytic support. Preferably, the crystalline aluminosilicate material has been cation-exchanged with a member selected from the group consisting of an alkaline earth metal, a rare earth metal, hydrogen, and a hydrogen precursor, such as ammonium ion, to reduce the alkali-metal content of the aluminosilicate material to a level that is less than 1 weight percent, calculated as the metal.

Such multi-metallic catalysts may also contain a combined halogen. Suitable combined halogens are chlorine and fluorine. The preferred combined halogen is chlorine. The halogen may be present in an amount of 0.1 weight percent to about 2 weight percent, based upon the total weight of the catalyst. Preferably, the halogen is present in an amount of about 0.1 weight percent to about 1 weight percent, based upon the weight of the catalyst.

The multi-metallic catalysts may be prepared in various ways. For example, a soluble compound of the hydrogenation metal or soluble compounds of the hydrogenation metals and a soluble compound of another metal, such as rhenium or gallium, may be added to a sol or gel of the refractory inorganic oxide. This composition may be thoroughly blended and the sol or gel mixture may be subsequently co-gelled by the addition of dilute ammonia. The resulting co-gelled material may then be dried and calcined. If a crytalline aluminosilicte material is to be a component of the catalytic composition, it may be added in a finely divided form to the sol or gel of the refractory inorganic oxide and suitble compounds of the hydrogenation metal or metals and other metals may be added thereto, and the resulting composition may then be thoroughly blended prior to co-gelling, drying, and calcining. In another method of preparation, the refractory inorganic oxide is gelled, dried, pelleted, calcined, and cooled, and the resulting composition is then impregnated with one or more solutions of the hydrogenation component(s) and other metals, such as rhenium or gallium. Suitable calcination conditions comprise a temperature in the range of about 900° F. to about 1,100° F. and a calcination time of about 1 to about 20 hours. Suitable drying conditions comprise a temperature in the range of about 200° F. to about 400° F. and a drying time of about 3 to about 30 hours. Preferably, drying conditions comprise a temperature of about 250° F. for about 8 to about 16 hours and calcination conditions comprise a temperature of about 1,000° F. for about 2 to about 6 hours. The combined halogen may be incorporated into the catalytic composition as a halide of the hydrogenation metal, or as a halogen acid, or a halide salt.

Reforming processes are employed to convert a feedstock which is a member selected from the group consisting of a virgin naphtha, a cracked naphtha, a hydrocarbon fraction boiling in the gasoline boiling range, and mixtures thereof. A reforming process may also be used to reform a partially-reformed naphtha and other hydrocarbon streams. A naphtha will exhibit a boiling range of about 70° F. to about 500° F., preferably, about 180° F. to about 400° F. The gasoline boiling range comprises temperatures of about 120° F. to about 420° F., preferably, about 140° F. to about 380° F. The partially-reformed hydrocarbon streams will exhibit unleaded research octane numbers within the range of about 75 to 95.

Since many of the above feedstocks may contain apprecible amounts of nitrogen and sulfur compounds, which are deleterious to platinum-containing reforming catalysts, it is preferred that the feedstock in such case be subjected to a suitable hydrodesulfurization and/or hydrodenitrogenation treatment, such as hydrofining, prior to its use in the reforming process in order to reduce both the nitrogen and sulfur levels to tolerable limits.

Typical operating conditions for a reforming process employing a multi-metallic catalyst comprise an average catalyst temperature of about 700° F. to about 1,050° F., a pressure of about 50 psig to about 1,000 psig, a weight hourly space velocity (WHSV) of about 0.5 to about 10 weight units of hydrocarbon per hour per weight unit of catalyst, and a hydrogen addition rate of about 1,500 standard cubic feed of hydrogen per barrel of hydrocarbon (SCFB) to about 15,000 SCFB. Preferred reforming conditions comprise an average catalyst temperature of about 850° F. to about 950° F., a pressure of about 50 psig to about 300 psig, a WHSV of about 1 to about 8 weight units of hydrocarbon per hour per weight unit of catalyst, and a hydrogen addition rate of about 2,000 SCFB to about 10,000 SCFB. These operating conditions are appropriate for each of the reactors in the reforming system.

The reforming process can be carried out in any of the conventional types of equipment known to the art. One may, for example, employ a catalyst in the form of pills, pellets, granules, broken fragments, or various special shapes, disposed as one or more fixed beds within one or more reaction zones, and the charging stock may be passed therethrough in the liquid, vapor, or mixed phase, and in either upward or downward flow or radial flow. Alternatively, the catalysts may be in a suitable form for use in moving beds, in which charging stock and catalyst are passed in co-current or countercurrent flow; or the catalysts may be used in fluidized-solid processes, in which the charging stock is passed upward through a turbulent bed of finely divided catalyst; or they may be employed in the suspensoid process, in which the catalyst is slurried in the charging stock and the resulting mixture is conveyed into the reaction zone. A fixed-bed reforming process is exemplified by Ultraforming (*Petroleum Engineer*, VOLUME XXVI, No. 4, April, 1954, at Page C-35).

A typical reforming system comprises 3 or more reactors, each reactor containing one or more fixed beds of catalyst disposed therein. The reaction products from any of the foregoing processes are removed from the reaction zones and fractioned to recover the various components thereof. The hydrogen and uncoverted materials and recycled as desired; the excess hydrogen produced in the reformer conveniently being utilized in the hydrodesulfurization of the feed.

Unwanted proucts in the reforming of petroleum hydrocarbon streams are light hydrocarbon gases and coke. Such products and other compounds, such as polynuclear aromatics and heavy hydrocarbons, may result in coke. As the operation progresses, a substantial amount of coke accumulates on the surface of each of the catalyst particles, resulting in an increasingly rapid rate of catalyst deactivation. Consequently, the coke must be removed periodically from the surface of the catalyst. Such coke removal may be accomplished through a coke-burn treatment wherein the coked catalyst is contacted with an oxygen-containing gas at selected temperatures. Typically, the gas will contain oxygen within the range of about 1.0 volume percent to about 21 volume percent. The concentration of oxygen in the gas should be maintained at a level which will not result in the production of temperatures that will be in excess of 1,100° F., preferably, in excess of 1,050° F.

In general, a reforming process is operated as a semi-regenerative process, a moving-bed process, or as a regenerative or cyclic process. In a semi-regenerative reforming system, the flow of hydrocarbons is stopped to all of the reactors and the catalyst in each of the reactors is regenerated. In a moving-bed regenerative system, catalyst is periodically withdrawn for regeneration and the regenerated catalyst is returned to the reactor. In a cyclic reforming system, one of the reactors is removed from the system and is replaced by an auxiliary reactor, which is known as a swing reactor. Reforming of petroleum hydrocarbons continues in such a system while catalyst in the reactor that has been removed from the system is regenerated. When the catalyst in the removed reactor has been regenerated, the reactor replaces the swing reactor in the system. The swing reactor can then be employed as a replacement for another reactor in the sytem in order that the latter vessel can be removed from the system while its catalyst is being regenerated.

Typical conditions that may be employed during the sulfiding method of the present invention comprise a temperature of about 350° F. to about 470° F., a pressure of about 0 to about 1,000 psig, a sulfur-carrying-gas flow rate of about 0.25 to about 100 SCF of gas per pound of catalyst, and a concentration of sulfur in the sulfur-carrying gas of about 0.01 to about 10 moles of sulfur per 100 moles of gas. The conditions are to be employed so that their combination will provide a sulfur concentration on the catalyst of about 0.1 to about 2.5 moles of sulfur per mole of active metal. No specific time is required for the sulfiding, although it must be sufficient to provide a sulfur concentration on the catalyst of about 0.1 to about 2.5 moles of sulfur per mole of active metal. It is preferred that it be conducted for a period of time of at least 20 minutes.

If the hydrogen-rich gas is being employed as a once-through gas, the flow rate of the sulfur-carrying gas will be within the range of about 0.25 to about 1 SCF of gas per pound of catalyst. In such case, the sulfur concentration in the sulfur-carrying gas may fall within the range of about 0.1 to about 10 moles of sulfur per 100 moles of gas. On the other hand, if the gas is being recycled in the sytem, the flow rate of the sulfur-carrying gas will be within the range of about 0.25 to about 100 SCF of gas per pound of catalyst and the sulfur concentration in the sulfur-carrying gas may be within the range of about 0.01 to about 10 moles of sulfur per 100 moles of gas.

As mentioned hereinabove, the method for sulfiding a catalyst, which method is provided by the present invention, may be used conveniently as the sulfiding pretreatment step in a method for starting-up of a reforming process unit that uses a bi-metallic or multi-metallic catalyst described hereinabove, that is, a method for initiating the reforming of a petroleum hydrocarbon feedstock in a reforming reaction zone containing a multi-metallic catalyst or a bi-metallic catalyst. The method may be used to sulfide the catalyst in all reactors of a system, if they all contain bi-metallic or multi-metallic catalyst; or it may be used to sulfide the catalyst in less than all reactors, even in a minimum of only one reactor, if such reactors or reactor constitute the only reactors or reactor in the system having the bi-metallic or multi-metallic catalyst and the system is a semi-regenerative system containing fresh or regenerated catalyst or a regenerative system containing fresh catalyst.

According to the present invention, there is provided also a method for initiating the reforming of a petroleum hydrocarbon feedstock in a reforming reaction zone containing a multi-metallic catalyst, the various metals of said catalyst comprising the total active metal of said catalyst. One embodiment of this method comprises introducing a stream of hydrogen-rich gas containing light hydrocarbons into said reaction zone at a pressure of about 0 to about 1,000 psig, passing said stream through said reaction zone, adjusting the temperature in said reaction zone to a value of about 350° F. to about 470° F., injecting a sulfur-containing compound into said stream up-stream from said catalyst in order to provide a sulfur-carrying gas, contacting said catalyst with said sulfur-carrying gas at said temperature and at a gas flow rate of about 0.25 to about 100 SCF of gas per pound of catalyst for a time that is sufficient to provide a sulfur concentration on said catalyst of about 0.1 to about 2.5 moles of sulfur per mole of total active metal, when sufficient sulfiding has occurred, discontinuing the injection of said sulfur-containing compound into said stream, adjusting the temperature, pressure, and hydrogen-rich-gas flow rate in said reaction zone to values that are to be used during the reforming operation, and introducing said feedstock into said reaction zone. A second embodiment of this method comprises introducing a stream of hydrogen-rich gas containing light hydrocarbons into said reaction zone at ambient temperature and a pressure of about 0 to about 1,000 psig, passing said stream through said reaction zone, raising the temperature of said reaction zone to a value of about 350° F. to about 470° F., injecting a sulfur-containing compound into said stream up-stream from said catalyst in order to provide a sulfur-carrying gas, contacting said catalyst with said sulfur-carrying gas at said temperature of about 350° F. to about 470° F. and at a gas flow rate of about 0.25 to about 100 SCF of gas per pound of catalyst for a time that is sufficient to provide a sulfur concentration on said catalyst of about 0.1 to about 2.5 moles of sulfur per mole of activve metal, when sufficient sulfiding has occurred, discontinuing the injection of said sulfur-contining compound into said stream, adjusting the temperature, pressure, and hydrogen-rich-gas flow rate in said reaction zone to values that are to be used during the reforming operation, and introducing the feedstock into said reaction zone. In either of these embodiments, the preferred sulfur-containing compound is dimethyl sulfide. Moreover, the sulfur concentration of the sulfur-carrying gas is about 0.01 to about 10 moles of sulfur per 100 moles of gas.

The method for sulfiding and the method for starting up a reformer that are provided by the present invention employ a hydrogen-rich gas that contains light hydrocarbons. Therefore, they employ an impure hydrogen stream and can be used in those refineries which do not have access to a source of pure hydrogen. Recycle gas or absorber off-gas are suitable hydrogen-rich gas streams that may be employed in the methods of the present invention. Such gases contain from about 70 to about 85 mole percent hydrogen and such light hydrocarbons as methane, ethane, and propane. Typically, the recycle gas from another reformer may be employed as the hydrogen-containing gas. Hence, these methods are conveniently and advantageously employed in a refinery having two or more reformers.

According to one embodiment of the sulfiding method of the present invention, the method comprises passing a stream of a hydrogen-rich gas containing light hydrocarbons over a multi-metallic catalyst at a temperature of 350° F. to about 470° F., injecting a sulfur-containing compound into said stream up-stream from said catalyst in order to provide a sulfur-carrying gas having a sulfur concentration of about 0.01 to about 10 moles of sulfur per 100 moles of gas, and contacting said catalyst with said sulfur-carrying gas at said temperature and at a gas flow rate of about 0.25 to about 100 SCF of gas per pound of catalyst for at least 20 minutes. The multi-metallic catalyst may have rhenium as one of its metals. It may be a bi-metallic catalyst, such as a platinum-rhenium catalyst. If the catalyst is a platinum-rhenium catalyst, it is sulfided to contain about 0.1 to about 2.5 moles of sulfur per mole of active metal (platinum plus rhenium).

The sulfiding of the multi-metallic or bi-metallic catalyst may be conducted conveniently at a pressure within the range of about 0 to about 1,000 psig. In fact, the sulfiding may be conducted at the same pressure that will be employed in the subsequent reforming operation.

In this method, the hydrogen-rich gas containing light hydrocarbons may be first passed over and through the bed of catalyst to be sulfided at a low temperature, possibly ambient temperature. Such contacting of the catalyst with the gas may be carried out from a very short time, less than 0.5 hour, to 1 or 2 hours. Then the catalyst is heated to a temperature of about 350° F. to about 470° F. This increase in temperature may be the result of heating the gas passing over the catalyst to the desired temperature and permitting the heated gas to provide the necessary heat for the catalyst. The heating may be conducted over a period of time that extends from about 1 hour to about 8 hours.

When the catalyst is at the prescribed temperature, a sulfur-containing compound is introduced or injected into the stream of the hydrogen-rich gas up-stream from the catalyst to provide a sulfur-carrying or sulfur-containing gas, i.e., a gas which contains sulfur and carries the sulfur as the gas passes through the reactor. In this way, the sulfur contacts the catalyst that is deposed in the vessel and is deposited upon the catalyst.

A preferred sulfur-containing compound is dimethyl sulfide. While hydrogen sulfide may be a sulfiding agent, it is not the preferred sulfide agent because it has an extremely high toxicity, which requires the use of extensive safety devices. Other sulfur-containing compounds that may be employed for this pre-sulfiding treatment of the catalyst include butyl mercaptan, dimethyl disulfide, ethyl mercaptan, propyl mercaptan, and carbon disulfide.

While the sulfiding step of the method of the present invention may be conducted for a relatively short period of time, it is believed that is should be at least 20 minutes in length. It may extend over a period of about 8 hours. The time required will be dictated by the gas flow rate and the concentration of the sulfur in the gas. The gas flow rate may vary between about 0.25 and about 100 SCF of gas per pound of catalyst, while sulfur may be present in the hydrogen-rich gas in a concentration of about 0.01 to about 10 moles of sulfur per 100 moles of gas.

At the completion of the sulfiding step, when employed in the start-up method disclosed herein, the injection or introduction of the sulfur-containing compound into the stream of hydrogen-rich gas is terminated while the passing of the hydrogen-rich gas over the catalyst is continued. If the pressure, temperature, and gas flow rate are not at the values which will be employed during the reforming operation, appropriate adjustments must be made. The feedstock to be reformed is then introduced into the system.

EXAMPLE 1

The start-up method of the present invention is exemplified by the following case. A semi-regenerative reformer having a capacity of 20,000 barrels of feedstock per day and 3 reactors is loaded with 150,000 pounds of catalyst. The catalyst comprises 0.4 weight percent platinum and 0.4 weight percent rhenium on a catalytically active alumina promoted with 0.7 weight percent combined chlorine. After the system has been purged with an inert gas, reformer off-gas (about 83 vol. percent hydrogen) from an adjacent reformer is introduced into the reaction zone of this reformer at ambient temperature and a pressure of 150 psig and is circulated through the 3 reactors of the reaction zone with the recycle gas compressor at a gas flow rate of about 2,000 SCF per barrel of capacity. This gas is passed through the reaction zone and while the gas flow is continued, the temperature in the reaction zone is raised from ambient temperature to about 400° F. This adjustment in temperature is completed in about 3 hours. Dimethyl sulfide is injected into the hydrogen-rich gas stream prior to each reactor in equal amounts to provide a sulfur concentration in the gas of 0.07 mole of sulfur per 100 moles of gas. The resultant sulfur-carrying gas is passed over the catalyst for 20 minutes. After this treatment, the catalyst contains about 0.5 mole of sulfur per mole of platinum plus rhenium. The injection of the dimethyl sulfide into the hydrogen-rich gas stream is then discontinued. With the hydrogen-rich gas passing through the reaction zone, the temperature is increased from about 400° F. to the temperature that will be used during the subsequent reforming operation. Appropriate adjustments to the pressure and gas flow rate of the hydrogen-rich gas are made in order to achievve those values that will be employed during the subsequent reforming operation. The naphtha to be reformed is then introduced into the reaction zone and, in the absence of hot spots, the reforming operation is permitted to continue.

EXAMPLE 2

A series of tests was conducted to determine at what temperature the onset of hydrocracking of n-butane occurs, when a catalyst comprising platinum is employed. Each test was performed in a stainless-steel pulse micro-reactor system. A 0.25-gram sample of catalyst was used in each test. The catalyst contained 0.37 wt.% platinum, 0.37 wt.% rhenium, and 0.74 wt.% combined chlorine on a gamma-alumina support. The catalyst existed in the form of 20-60 mesh (U.S. Sieve Series) particles. In each test, a 0.25-cc pulse of n-butane in a stream of hydrogen was pased over the catalyst sample at approximately atmospheric pressure. The contact time was approximately 0.5 second and the hydrogen flow rate was 40 cc/min. The resulting product was passed into an in-series gas-chromatographic column comprising a 6-foot length of Silicone SE-30 on celite. Adequate separation of the hydrocarbon gases was obtained and the extent of hydrocracking was determined.

Catalyst Sample No. 1 was not sulfided. This sample, as well as all of the other catalyst samples of this series of tests, did not receive an initial high-temperature reduction treatment. Each of the other catalyst samples, Samples Nos. 2 through 6, were sulfided and tested according to the following sequence of steps: passing hydrogen over the catalyst at the specified flow rate; heating the reaction zone to the temperature at which sulfiding was to be performed while hydrogen flow was maintained; upon reaching the desired temperature, injecting dimethyl sulfide into the stream of flowing hydrogen up-stream from the catalyst; subsequently, adjusting the temperature of the catalyst, while hydrogen was flowing, to the temperature at which the hydrocracking of n-butane was to be conducted; upon reaching the desired hydrocracking temperature, introducing the pulse of n-butane into the stream of flowing hydrogen up-stream from the catalyst; and passing the product stream through the gas-chromatographic equipment. In the case of Catalyst Sample No. 1, which was not sulfided, the catalyst was heated up to the desired hydrocracking temperature in the presence of flowing hydrogen and the hydrocracking test was conducted as described hereinabove.

Catalyst Sample No. 2 was sulfided at a temperature of 25° C. (77° F.); Catalyst Sample No. 3, at a temperature of 100° C. (212° F.); Catalyst Sample No. 4, at a temperature of 150° C. (302° F.); Catalyst Sample No. 5, at a temperature of 200° C. (392° F.); and Catalyst Sample No. 6, at a temperature of 350° C. (662° F.).

The data obtained from the tests were treated by assuming first order kinetics with respect to the disappearance of n-butane. The relative rate of hydrocracking, R, was calculated by the integrated form of a first-order rate equation:

$$R = \log_{10}\left[\frac{100}{100 - \% \text{ n-butane hydrocracked.}}\right]$$

The results were plotted in the accompanying figure. Appropriate data were obtained from this figure by interpolation and are presented in the following table.

| Catalyst No. | Temp. Required to Obtain % Hydrocracking, ° F. | | |
| --- | --- | --- | --- |
| | 5% | 10% | 25% |
| 1 | 478 | 508 | 550 |
| 2 | 511 | 545 | 604 |
| 3 | 498 | 532 | 583 |
| 4 | 493 | 527 | 583 |
| 5 | 738 | 790 | 875 |

-continued

| Catalyst No. | Temp. Required to Obtain % Hydrocracking, ° F. | | |
|---|---|---|---|
| | 5% | 10% | 25% |
| 6 | 816 | 881 | 978 |

The results of this series of tests indicate that the sulfiding must be done at a temperature of about 200° C. (392° F.) or above for adequate hydrocracking inhibition to occur. Sulfiding at a temperature of 150° C. (302° F.) appears to be unsatisfactory. Moreover, the onset of hydrocracking (assumed to be 5% hydrocracking), when the unsulfided catalyst, Catalyst Sample No. 1, was used, was about 470° F.

While hydrocracking is initiated in these tests at a temperature of about 400° F., it is recommended that the sulfiding of the multi-metallic catalyst be done at a temperature that is not lower than 50° F. below the temperature at which hydrocracking is initiated in order to provide sufficient and proper sulfiding of the catalyst.

In view of the above, the sulfiding of the catalyst should be carried out at a temperature that is within the range of about 350° F. to about 470° F.

The above examples are presented for purposes of illustration only and are not intended to limit the scope of the present invention as set our hereinafter in the claims.

It has been found that the above-described sulfiding method and start-up technique will conveniently and advantageously minimize or eliminate the excessive hydrocracking that occurs if a multi-metallic or bi-metallic catalyst is subjected to a hydrogen-rich gas containing hydrocarbons during sulfiding.

What is claimed is:

1. A method for sulfiding a multi-metallic reforming catalyst when employing a hydrogen-rich gas containing light hydrocarbons during said sulfiding, the various metals of said catalyst comprising the total active metal of said catalyst, which method comprises passing a stream of said gas over said catalyst at a temperature of about 350° F. to about 470° F., injecting a sulfur-containing compound into said stream up-stream from said catalyst in order to provide a sulfur-carrying gas, and contacting said catalyst with said sulfur-carrying gas at said temperature for a time that is sufficient to provide a sulfur concentration on said catalyst of about 0.1 to about 2.5 moles of sulfur per mole of total active metal.

2. The method of claim 1 wherein said sulfur-containing compound is dimethyl sulfide.

3. The method of claim 1 wherein one of the metals of said catalyst is rhenium.

4. The method of claim 1 wherein the flow rate of said sulfur-carrying gas is within the range of about 0.25 to about 100 SCF of gas per pound of catalyst and said method is operated at a pressure of about 0 to about 1,000 psig.

5. The method of claim 1 wherein the concentration of sulfur in said sulfur-carrying gas is about 0.01 to about 10 moles of sulfur per 100 moles of gas.

6. The method of claim 4 wherein the flow rate of said sulfur-carrying gas is within the range of about 0.25 to about 1 SCF of gas per pound of catalyst.

7. The method of claim 4 wherein the concentration of sulfur in said sulfur-carrying gas is about 0.01 to about 10 moles of sulfur per 100 moles of gas.

8. The method of claim 7 wherein said sulfur-containing compound is dimethyl sulfide.

9. The method of claim 7 wherein one of the metals of said catalyst is rhenium.

10. The method of claim 9 wherein said sulfur-containing compound is dimethyl sulfide.

11. A method for sulfiding a multi-metallic reforming catalyst when employing a hydrogen-rich gas containing light hydrocarbons during said sulfiding, the various metal of said catalyst comprising the total active metal of said catalyst, which method comprises passing a stream of said gas over said catalyst at ambient temperature, increasing the temperature of said catalyst to a value of about 350° F. to about 470° F. while said gas is flowing over said catalyst, injecting a sulfur-containing compound into said stream up-stream from said catalyst in order to provide a sulfur-carrying gas, and contacting said catalyst with said sulfur-carrying gas at said temperature of about 350° F. to about 470° F. for a time that is sufficient to provide a sulfur concentration on said catalyst of about 0.1 to about 2.5 moles of sulfur per mole of total active metal.

12. The method of claim 11 wherein the flow rate of said sulfur-carrying gas is within the range of about 0.25 to about 100 SCF of gas per pound of catalyst and said method is operated at a pressure of about 0 to about 1,000 psig.

13. The method of claim 11 wherein said catalyst comprises a Group VIII noble metal and rhenium on a refractory inorganic oxide.

14. The method of claim 11 wherein the concentration of sulfur in said sulfur-carrying gas is about 0.01 to about 10 moles of sulfur per 100 moles of gas.

15. The method of claim 13 wherein said Group VIII noble metal is platinum, said refractory inorganic oxide is a catalytically active alumina, and said catalyst also contains a combined halogen.

16. The method of claim 13 wherein the flow rate of said sulfur-carrying gas is within the range of about 0.25 to about 100 SCF of gas per pound of catalyst and said method is operated at a pressure of about 0 to about 1,000 psig.

17. The method of claim 15 wherein the flow rate of said sulfur-carrying gas is within the range of about 0.25 to about 100 SCF of gas per pound of catalyst and said method is operated at a pressure of about 0 to about 1,000 psig.

18. The method of claim 16 wherein the concentration of sulfur in said sulfur-carrying gas is about 0.01 to about 10 moles of sulfur per 100 moles of gas.

19. The method of claim 17 wherein the concentration of sulfur in said sulfur-carrying gas is about 0.01 to about 10 moles of sulfur per 100 moles of gas.

20. The method of claim 18 wherein said sulfur-containing compound is dimethyl sulfide.

21. The method of claim 19 wherein said sulfur-containing compound is dimethyl sulfide.

22. A method for initiating the reforming of a petroleum hydrocarbon feedstock in a reforming reaction zone containing a bi-metallic catalyst or a multi-metallic catalyst, the various metals of said catalyst comprising the total active metal of said catalyst, which method comprises introducing a stream of hydrogen-rich gas containing light hydrocarbons into said reaction zone at a pressure of about 0 to about 1,000 psig, passing said stream through said reaction zone, adjusting the temperature in said reaction zone to a value of about 350° F. to about 470° F., injecting a sulfur-containing compound into said stream up-stream from said catalyst in order to provide a sulfur-carrying gas, contacting said catalyst with said said sulfur-carrying gas at said temperature and at a gas flow rate of about 0.25 to about 100 SCF of gas per pound of catalyst for a time that is sufficient to provide a sulfur concentration on said catalyst of about 0.1 to about 2.5 moles of sulfur per mole of total active metal, when sufficient sulfiding has occurred, discontinuing the injection of said sulfur-containing compound into said stream, adjusting the temperature, pressure, and hydrogen-rich-gas flow rate in said reaction zone to values that are to be used during the reforming operation, and introducing said feedstock into said reaction zone.

23. The method of claim 22 wherein said sulfur-containing compound is dimethyl sulfide.

24. The method of claim 22 wherein the concentration of sulfur in said sulfur-carrying gas is about 0.01 to about 10 moles of sulfur per 100 moles of gas.

25. The method of claim 22 wherein said catalyst comprises a Group VIII noble metal and rhenium of a refractory inorganic oxide.

26. The method of claim 25 wherein said Group VIII noble metal is platinum, said refractory inorganic oxide is a catalytically active alumina, and said catalyst also contains a combined halogen.

27. The method of claim 25 wherein the concentration of sulfur in said sulfur-carrying gas is about 0.01 to about 10 moles of sulfur per 100 moles of gas.

28. The method of claim 26 wherein the concentration of sulfur in said sulfur-carrying gas is about 0.01 to about 10 moles of sulfur per 100 moles of gas.

29. The method of claim 27 wherein said sulfur-containing compound is dimethyl sulfide.

30. The method of claim 28 wherein said sulfur-containing compound is dimethyl sulfide.

31. A method for initiating the reforming of a petroleum hydrocarbon feedstock in a reforming reaction zone containing a bi-metallic or a multi-metallic catalyst, the various metals of said catalyst comprising the total active metal of said catalyst, which method comprises introducing a stream of hydrogen-rich gas containing light hydrocarbons into said reaction zone at ambient temperature and a pressure of about 0 to about 1,000 psig, passing said stream through said reaction zone, raising the temperature of said reaction zone to a value of about 350° F. to about 470° F., injecting a sulfur-containing compound into said stream up-stream from said catalyst in order to provide a sulfur-carrying gas, contacting said catalyst with said sulfur-carrying gas at said temperature of about 350° F. to about 470° F. and at a gas flow rate of about 0.25 to about 100 SCF of gas per pound of catalyst for a time that is sufficient to provide a sulfur concentration on said catalyst of about 0.1 to about 2.5 moles of sulfur per mole of total active metal, when sufficient sulfiding has occurred, discontinuing the injection of said sulfur-containing compound into said stream, adjusting the temperature, pressure and hydrogen-rich-gas flow rate in said reaction zone to values that are to be used during the reforming operation, and introducing said feedstock into said reaction zone.

32. The method of claim 31 wherein said catalyst comprises a Group VII noble metal and rhenium on a refractory inorganic oxide.

33. The method of claim 31 wherein the concentration of sulfur in said sulfur-carrying gas is about 0.01 to about 10 moles of sulfur per 100 moles of gas.

34. The method of claim 31 wherein said sulfur-containing compound is dimethyl sulfide.

35. The method of claim 32 wherein said Group VIII noble metal is platinum, said refractory inorganic oxide is a catalytically active alumina, and said catalyst also contains a combined halogen.

36. The method of claim 32 wherein the concentration of sulfur in said sulfur-carrying gas is about 0.01 to about 10 moles of sulfur per 100 moles of gas.

37. The method of claim 35 wherein the concentration of sulfur in said sulfur-carrying gas is about 0.01 to about 10 moles of sulfur per 100 moles of gas.

38. The method of claim 36 wherein said sulfur-containing compound is dimethyl sulfide.

39. The method of claim 37 wherein said sulfur-containing compound is dimethyl sulfide.

* * * * *

UNITED STATES PATENT OFFICE
CERTIFICATE OF CORRECTION

Patent No. 4,048,058      Dated September 13, 1977

Inventor(s) PETERSEN, RICHARD D., and MIEVILLE, RODNEY L.

It is certified that error appears in the above-identified patent and that said Letters Patent are hereby corrected as shown below:

Column 1, line 49,    "pich up" should be --pick up--.

Column 4, line 42,    "aluminosilicte" should be --aluminosilicate--.

Column 5, line 29,    "feed" should be --feet--.

Column 9, line 6,    "that is" should be --that it--.

Column 10, line 1,    "platinum" should be --platinum and rhenium--.

Column 11, line 28,    "our" should be --out--.

Column 13, line 18,    "0.01to" should be --0.01 to--.

Column 13, line 21,    "rhenium of" should be --rhenium on--.

Column 14, line 21,    "Group VII" should be --Group VIII--.

at bottom of the figure, "/Kx10$^3$" should be --1/Kx10$^3$--.

Signed and Sealed this

Eleventh Day of November 1980

[SEAL]

Attest:

SIDNEY A. DIAMOND

Attesting Officer     Commissioner of Patents and Trademarks